United States Patent [19]
Greene et al.

[11] Patent Number: 5,217,691
[45] Date of Patent: Jun. 8, 1993

[54] NONENZYMATIC GLUCOSE TEST

[75] Inventors: Carmine Greene; Ibrahim A. Ismail, both of South Bend; Wen H. Wu, Elkhart, all of Ind.

[73] Assignee: Miles Inc., Elkhart, Ind.

[21] Appl. No.: 878,224

[22] Filed: May 4, 1992

Related U.S. Application Data

[60] Continuation of Ser. No. 708,209, May 31, 1991, abandoned, which is a division of Ser. No. 256,559, Oct. 13, 1988, Pat. No. 5,116,763, which is a continuation of Ser. No. 885,535, Oct. 2, 1986, abandoned, which is a continuation of Ser. No. 736,300, May 30, 1985, abandoned, which is a continuation-in-part of Ser. No. 673,184, Nov. 19, 1984, abandoned.

[51] Int. Cl.$^5$ ............................................. G01N 21/01
[52] U.S. Cl. ........................................ 422/56; 422/55; 422/57; 422/61; 436/95
[58] Field of Search ................... 422/55, 56, 57, 61; 436/95

[56] References Cited

U.S. PATENT DOCUMENTS 4,568,647  2/1986  Sanford .................................. 422/56

Primary Examiner—Robert J. Warden
Assistant Examiner—Timothy M. McMahon
Attorney, Agent, or Firm—Roger N. Coe

[57] ABSTRACT

The invention provides a nonenzymatic method useful for the semiquantitative determination of glucose, a test composition and test device. Glucose concentration in an aqueous test sample can be determined by preparing a test solution by contacting an aqueous test sample and a dihydroxide component, at an initial pH above 6.5, capable of forming a complex with glucose which complex formation releases a proton, and determining the final pH of the test solution. The invention also provides a self-indicating device format which allows the determination of glucose concentration by merely counting the number of pads which have changed color. No comparison to a color chart is required. The glucose test of the present invention is free of the interferences found in enzymatic glucose tests.

3 Claims, 1 Drawing Sheet

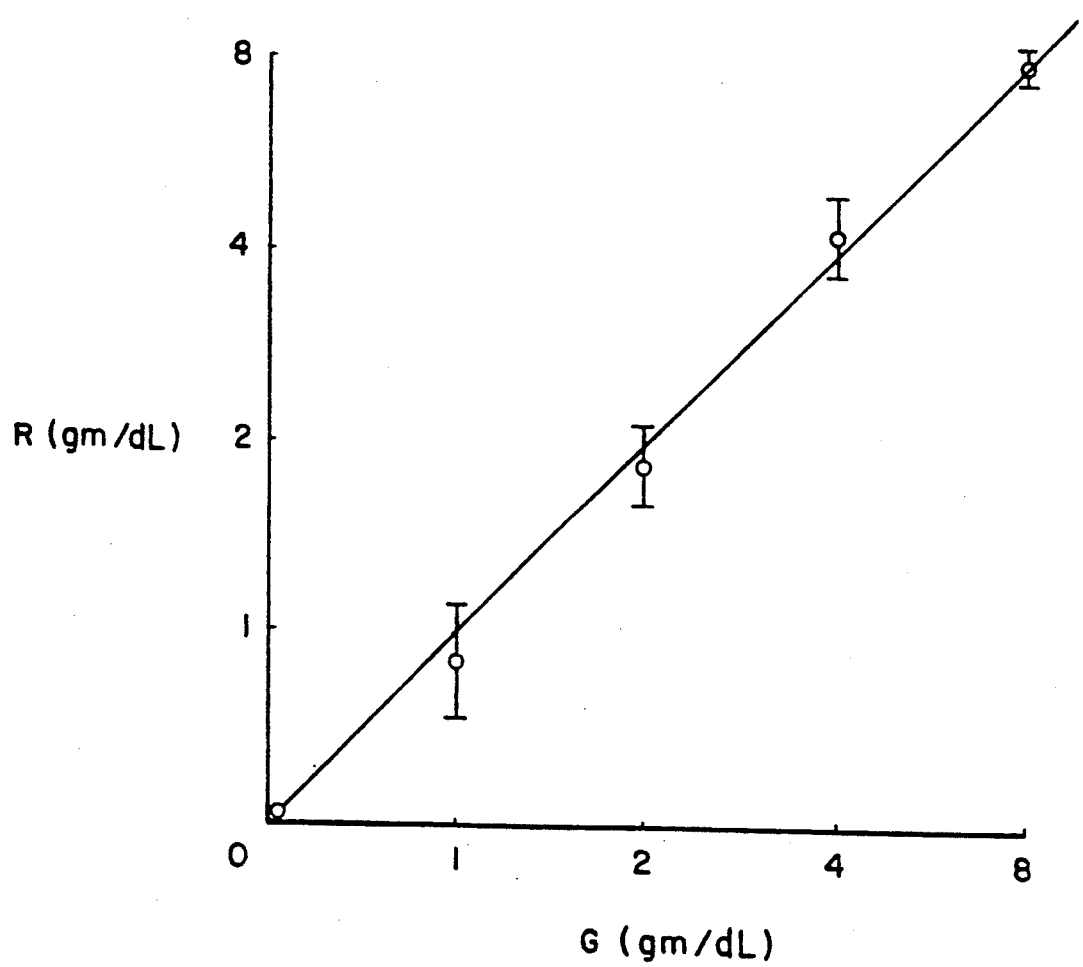

NONENZYMATIC GLUCOSE TEST

RELATED APPLICATIONS

This application is a continuation of application Ser. No. 708,209, now abandoned, filed on May 31, 1991; which is a division of Ser. No. 256,559, filed Oct. 13, 1988, now U.S. Letters Pat. No. 5,116,763; which is a continuation of Ser. No. 885,535, filed Oct. 2, 1986, now abandoned; which is a continuation of Ser. No. 736,300, filed May 30, 1985, now abandoned; which is a continuation-in-part of Ser. No. 673,184, filed Nov. 19, 1984, now abandoned.

FIELD OF THE INVENTION

The invention relates to nonenzymatic methods for the semiquantitative determination of glucose in general and to nonenzymatic diagnostic compositions for the colorimetric determination of glucose in aqueous test samples in particular.

UTILITY

Determination of glucose concentration in aqueous solution is useful industrially in the sugar industry and medically. Medically, the semiquantitative determination of glucose in body fluids, such as urine or blood, is of importance as a public health measure to screen large numbers of people for diabetes, and is of particular importance for diabetic patients who must control their sugar intake Because early diagnosis and continued control are so important in diabetes, a glucose test, to be of greatest value to the physician, clinician or home diabetic user must be rapid and simple enough to perform conveniently and yet sensitive enough to reflect meaningful variations in urine or blood glucose.

Semiquantitative determination of high range glucose, defined herein as glucose concentrations of 1,000 milligrams per deciliter (mg/dL) and above, is important because urine glucose concentration in diabetic patients can range up to 5,000 mg/dL or higher. The quantitative estimation of high urine glucose concentrations is important for at least two reasons. First, in emergency situations it is important to determine whether a state of unconsciousness can be attributed to diabetic coma, which would be indicated by a high urine glucose concentration. Second, urine glucose levels become elevated if an insufficient amount of insulin has been administered. A test which can estimate high urine glucose concentrations therefore has utility in the therapeutic monitoring of insulin requirements.

INFORMATION DISCLOSURE

Most diagnostic testing for glucose presently performed clinically is based on the enzymatic action of glucose oxidase on $\beta$-D-glucose:

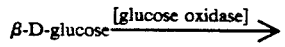

$$H_2O_2 + \text{gluconic acid} + O_2 + H_2O$$

and the resultant oxidation of a chromogen (Cr) to its oxidized state (Cr*) which is visually detectable by a color change:

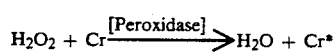

Great convenience is obtained when the test device can be used semiquantitatively to determine glucose levels by visual comparison of the color, developed after contact with a test sample, with an appropriate color chart. Such semiquantitative determinations can also be performed instrumentally by measuring the reflectance of a reacted device. However, as the concentration of glucose increases above 1,000 mg/dL the color of most chromogens used in enzymatic systems is so dark as to preclude distinguishing high concentration levels. U.S. Pat. No. 4,340,669 describes the observed results with o-tolidine, tetramethylbenzidine and tetraethylbenzidine as chromogen at 0, 50, 100, 250, 500 and 1,000 mg/dL glucose in the fluid being tested. Each of these chromogens turns from yellow to bright green when the concentration of glucose increases from 0 to 50 mg/dL. As the concentration of glucose increases above 500 mg/dL the color of the oxidized chromogen darkens so that the observed colors of the respective chromogens were olive-black, black and deep green. This observation highlights a problem with the semiquantitative enzymatic determination of glucose in aqueous fluids, that is at high concentrations known chromogens appear black or very dark green thereby limiting the utility of the test devices for determination of glucose above 500 mg/dL. While the problem is not so acute if the color change is determined instrumentally, it nonetheless still exists. Some success in increasing the visually readable range of glucose with enzymatic compositions has been achieved by the addition of secondary chromogens such as m-anisidine (U.S. Pat. No. 4,340,669).

In addition to poor color differentiation at high glucose concentrations, enzyme-based glucose tests are interfered with by ascorbic acid (vitamin C) present in body fluids, are expensive and are subject to stability problems.

Nonenzymatic methods for measuring glucose have also been used. These include instrumental methods based on a measuring electrode (see, for example, U.S. Pat. No. 4,127,448) and even a non-invasive automatic glucose sensor system which scans the patient's eye for radiation transmitted through the cornea (see U.S. Pat. No. 3,958,560). U.S. Pat. No. 4,278,438 discloses a method and apparatus for the analysis of saccharides. An alkylene polyamine prepared in a borate buffer is used to elute saccharides from a chromatography column.

U.S. pat. No. 4,371,374 discloses a method of monitoring blood glucose by separating and quantitating nonenzymatic glycoslyated amino acids, peptides or mixtures thereof by treating a urine sample with a suitable boronic acid to complex the glycosylated compounds, separating them and analyzing the separated complexed material.

The present invention does not require elaborate equipment, but nevertheless allows the determination of glucose up to any desired concentration level, by use of the complexation of glucose with a dihydroxide component. Complexation of sugars with boron and alkali earth dihydroxides has been reported [S. A. Barker et al., *Carbohydrate Research*, 26 (1973) 33-40; N. Roy et al., *Carbohydrates Research*, 24 (1972) 180-183]; but this phenomenon has not been used to solve the problem of semiquantitatively determining glucose concentration in an aqueous test samples.

A preferred embodiment of the present invention provides a self-indicating device for the determination of glucose based on the use of the complexation of glucose with a dihydroxide component. The self-indicating device of this invention permits a visual determination of the concentration of glucose without comparison to a color indicator chart.

A disposable indicator device for the determination of cholesterol was disclosed in U.S. Pat. No. 4,042,329. The closed device provides an indication of the concentration of cholesterol in a given biological fluid which is directly readable in notation format.

DESCRIPTION OF THE DRAWING

The drawing indicates the reproducibility of visual determinations of glucose concentration with a nonenzymatic test device of the present invention. Test devices formulated for the semiquantitative determination of high range glucose were contacted with contrived urine test samples containing from 1 gm/dL to 8 gm/dL glucose. The graph verifies the linear relationship of glucose concentration, G, in gm/dL with device reading, R, in gm/dL. The test devices were prepared by pretreating a paper carrier matrix with a borate buffer prepared from phenylboronic acid prior to incorporation of a test composition comprising a borate buffer prepared from boric acid and a pH indicator.

SUMMARY OF THE INVENTION

The invention provides a method for semiquantitatively determining glucose in an aqueous test sample, a test composition useful for such a determination, a test device and a method for its preparation and use. The method for determining glucose in an aqueous test sample, comprises the steps of: a) preparing a test solution by contacting the aqueous test sample and a dihydroxide component, at an initial pH above 6.5, capable of forming a complex with glucose which complex formation releases a proton; and b) determining the final pH of the test solution. The test composition comprises: a) a dihydroxide component, at an initial pH above 6.5, capable of forming a complex with glucose which complex formation releases a proton; and b) a pH indicator capable of providing a detectable colorimetric response in a pH range of from about pH 6.5 to about pH 12. A carrier matrix can be incorporated with the test composition to provide a particularly convenient test device format. A preferred embodiment is a self-indicating test device.

DETAILED DESCRIPTION OF THE INVENTION

A number of carbohydrates containing a cisdiol grouping form a variety of complexes with compounds containing a dihydroxide group. (See, for example, N. Roy et al., Carbohydrates Research 24 (1972) 180-183, and S. A. Barker et al., Carbohydrate Research, 26 (1973) 33-40). It has been found that this complex formation can be used to provide a semiquantitative determination of the concentration of glucose in an aqueous test sample by preparing a test solution by contacting the sample with a dihydroxide, at an initial pH above 6.5, capable of forming a complex with glucose, which complex formation releases a proton into solution, and determining the final pH of the test solution.

Suitable dihydroxides include those of barium, boron, calcium, magnesium and strontium. [Ba(OH)$_2$, Z-B(OH)$_2$, Ca(OH)$_2$, Mg(OH)$_2$ and Sr(OH)$_2$]. Dihydroxides of boron and strontium are preferred. Particularly preferred are boron dihydroxides of the general formula

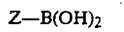

$$Z-B(OH)_2$$

wherein Z is an electron withdrawing such as a nitro group or electron stabilizing group such as a hydroxyl or arene group. Where Z is a hydroxyl group the boron dihydroxide is boric acid. Suitable boron dihydroxides include boric acid phenylboronic acid, p-nitrophenylboronic acid, 4-methoxyphenylboronic acid and α-naphthylboronic acid, naphthylboronic acid as well as other areneboronic acids and their derivatives. An arene group is defined as any hydrocarbon group containing at least one aromatic ring. These groups are useful in the present invention provided the anionic negative form of the dihydroxide can be stabilized by electron resonance over the aromatic ring. For example, the compound phenylboronic acid where Z is a phenyl group is particularly useful in the invention. In addition arene derivatives, such as p-nitrophenylboronic acid, which contain electron withdrawing groups as substituents on the aromatic ring are also useful.

Glucose can be determined by preparing a test solution with an aqueous test sample and a dihydroxide component at an initial pH above 6.5, capable of forming a complex with glucose, which complex formation releases a proton, and measuring the final pH of the test solution. The test solution can usually be formed by simply contacting the dihydroxide with the aqueous test sample.

The barium, boron, calcium, magnesium and strontium dihydroxides generally form 1:1 complexes with glucose. Therefore the ratio of dihydroxide to glucose in the test sample must be approximately one to one. To form a test solution of a boron dihydroxide, such as boric acid, in sufficient concentration to determine glucose concentrations of about 500 mg/dL or greater, it may be necessary to use a base such as potassium hydroxide or sodium hydroxide to dissolve the boron dihydroxide. An equivalent procedure would be the use of the salt form of boric acid as part of the hydroxide component. Obviously, other bases are also useful provided they do not interfere with the complex formation between the dihydroxide and glucose.

The final pH of the test solution can be measured conventionally with a pH meter or visually or instrumentally after the addition of a pH indicator.

The pH change which occurs with complex formation between the dihydroxide component and glucose, can be moderated by the addition of a buffer. A test composition which includes a buffer capable of moderating a pH change over the pH range of from about pH 6.5 to about pH 12 can be used to determine glucose over a wider concentration range than a test composition without such a buffer. Suitable buffers include tris(hydroxymethyl)aminomethane, commonly known as TRIS, N,N-bis(2-hydroxyethyl)glycine, commonly known as BICINE and N-2-hydroxyethylpiperazine-N'-2-ethanesulfonic acid, commonly known as HEPES. It is particularly convenient when using a boron dihydroxide such as boric acid or phenylboronic acid to use the buffer form as the dihydroxide component.

A borate buffer is defined as the mixture of the acid and base form of a Z-B(OH) compound. The equilibrium between the two forms can be shown schematically as:

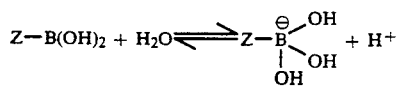

where Z can be any of the groups described previously.

The borate buffer can be prepared from boric acid (Z=OH) or from areneboronic acid derivatives such as phenylboronic acid or mixtures of Z—B(OH)$_2$ compounds by commonly used laboratory methods well known to those skilled in the art. For example, a solution of boric acid buffer can be prepared by titrating boric acid with a base such as sodium or potassium hydroxide to an initial pH within the buffering range of the Z—B(OH)$_2$ compound used. This buffering range is expected to fall between pH 6.5 to pH 12 for most Z—B(OH)$_2$ compounds. The buffer can also be prepared by adding equimolar parts of the acid and base forms of the dihydroxide and dissolving in water.

The choice of the initial buffer pH can affect the concentration range of glucose which can be determined with a particular test composition. For example, the effectiveness of the complexation of boron dihydroxide with glucose decreases as the pH of the solution falls below the pKa of the borate buffer. The addition of electron withdrawing substituents on a buffer prepared from an areneboronic acid derivative changes the pKa of the buffer and therefore its effective pH and complexing range. For example, boric acid, pKa 9.2, has a lower complexing capacity below about pH 7.0, while phenylboronic acid, pKa 8.8, will complex with glucose at a pH as low as 6.5. $p$-Nitrophenylboronic acid, pKa 7.4, has an even lower effective pH. A mixture of borate buffers, such as boric acid buffer and phenylboronic acid buffer, can extend the effective pH range of the borateglucose complexing and therefore the glucose concentration range which can be determined. When a boric acid buffer is used, an initial pH above 8.0 is preferred. For high range glucose determinations with a boric acid buffer, an initial pH above 9.0 is particularly preferred.

The buffer is most useful in a glucose determination when the initial pH is slightly above its pKa. The buffer can, or course, be supplied in a dry state by removal of water after the initial pH is set. The buffer is capable of providing that pH when reconstituted.

It is particularly convenient to provide a test composition for the determination of glucose including a dihydroxide as defined herein and a pH indicator capable of providing a detectable colorimetric response in the pH range of from about pH 6.5 to about pH 12. Any pH indicator which changes color within this pH range, or any combination of indicators, can be used. Useful indicators include m-cresol purple, cresol red, neutral red, thymol blue, phenophthalein, o-cresol phthalene, phenol red, bromothymol blue or Universal Indicator, a mixture of indicators available from Kodak. The test composition can be used to determine glucose concentration simply by contacting the composition and the aqueous test sample and observing the detectable colorimetric response produced.

A pH indicator changes color over a range of pH values. The pKa of an indicator represents approximately the midpoint of its color changes. The initial pH of the borate buffer chosen is related to which indicator is used. For example, m-cresol purple changes from purple at pH 9.0 to yellow at pH 7.4. At pH values above 9.0, the indicator remains purple or changes color very little with pH change. If an initial pH of 9.0 is used, a detectable response will be apparent with any pH change. If an initial pH of 9.2 or higher is used, the composition will not change color i.e., will not have a detectable response to glucose concentration, until the pH drops below pH 9.0. Therefore, the compositions utilizing m-cresol purple containing a buffer capable of providing an initial pH of 9.0 will be more sensitive to a lower glucose concentration than such compositions containing a buffer capable of providing an initial pH of 9.2. If a different pH indicator is used, another initial pH can be preferred. For example cresol red has a pH range between about 8.8 (red) and about 7.2 (yellow); a lower initial pH, such as pH 9.0, is then preferred for optimal performance in this test composition. The use of more than one indicator can provide a color change over a broader pH range and therefore over a broader glucose concentration range.

A test composition which is particularly suited for the determination of high range glucose (defined herein as at least 1,000 milligrams glucose per deciliter) is a borate buffer capable of moderating pH change in a pH range of from about pH 6.5 to about pH 12 and a pH indicator capable of providing a detectable colorimetric response in a pH range of from about pH 6.5 to about pH 12.

In a preferred composition prepared for high range urine glucose determinations, the borate buffer is a boric acid buffer prepared so that it is capable of providing an initial pH of about 9.2. This high initial pH avoids non-specific pH change and interference by urine pH and buffering capacity. The buffer so prepared can be provided in a dry state by lyophilization or simply dried to remove the water used to prepare the buffer.

Additional components such as wetting agents, stabilizers or thickeners can be added to the test composition provided they do not interfere with the complexation of the dihydroxide with glucose.

Any of these compositions can be provided in the form of a bottled reagent, a frangible capsule containing the test composition in reagent form, a pill or a tablet.

The test device, a preferred form of the invention, is prepared by treating a suitable carrier matrix with the test composition in the form of a liquid reagent and drying.

The carrier matrix can be any substance capable of being incorporated with the components of the test composition, as long as it is substantially inert with respect to the test composition, porous and/or absorbent relative to the aqueous sample to be tested. The expression "carrier matrix" refers to either bibulous or nonbibulous matrices which are insoluble in and maintain their structural integrity when exposed to water or to other physiological fluids. Suitable bibulous matrices which can be used include paper, cellulose, wood, synthetic resin fleeces, woven and nonwoven fabrics and the like. Nonbibulous matrices include glass fiber, polymer films and microporous membranes.

It is, therefore, to be appreciated that in producing a test device of the invention all such carrier matrix concepts can be employed, as can others. The matrix can also comprise a system wherein the composition ingredients are homogeneously combined in a fluid or semifluid state, which later hardens or sets, thereby incorporating the ingredients. Other matrix formats are contemplated, including the use of microporous membranes or polymer film matrices. Microporous membranes are available as preformed membranes or can be prepared by such techniques as phase inversion. Suitable polymer films can be produced with commercially available latex formulations based on latex polymer suspensions such as that formed from a 60:40 copolymer of styrene and butadiene. Other natural or synthetic polymers or mixtures thereof can also be used. Examples of such film formulations can be found in U.S. Pat. Nos. 3,630,957 and 4,312,834, incorporated herein by reference.

The presently preferred method of preparation is impregnating a bibulous carrier matrix, for example filter paper, with an aqueous solution of the composition and drying, followed by affixing the dried impregnated matrix to a support member. The impregnating solution is prepared so that it exhibits the desired initial pH. When a whole blood sample is to be tested, the dried impregnated carrier matrix can be coated to allow excess sample to be washed or wiped off. Drying can be accomplished by any means which will not deleteriously affect the incorporated composition, usually by means of an air oven. Incorporation can be accomplished by any method such as coating, dipping, spreading, spraying or printing which allows the carrier matrix to be incorporated wit the assay composition. The dried carrier matrix can thereafter be cut and mounted on one end of a support member, for example, a rigid or semirigid polystyrene film strip. The dihydroxide component and/or buffer are in such a form as to be capable of providing an initial pH above 6.5 at the surface of the incorporated carrier when the carrier is wetted. The pH of the wetted incorporated carrier can be measured with surface electrodes. The term "incorporated carrier" refers to a carrier matrix incorporated with the test composition and dried. When a transparent film strip is used, instrumental reading of a reacted device can be accomplished from either side of the strip. Mounting of the paper on the strip can be accomplished through use of a double-faced adhesive tape, such as that commercially available from the 3M Co., St. Paul, MN., under the trademark DOUBLE STICK ®.

When a paper carrier matrix is used with a boric acid buffer, it can be advantageous to treat the paper with an aqueous solution of a second borate buffer such as that prepared from phenylboronic acid at an initial pH above 6.5, prior to incorporation of the test composition containing the borate buffer. It is speculated that such a pretreatment prevents possible interaction of the paper with the borate buffer in the test composition.

Concentration ranges for components in the reagent solution used to prepare a solid state test device are as follows:

|  | working | preferred |
| --- | --- | --- |
| borate buffer | 0.1–0.9M | 0.1–0.4M |
| pH indicator | 0.025–0.2% | 0.04–0.15% |

These concentration ranges and relative concentrations of components are viable whether the solution is an aqueous impregnating solution or a polymer suspension. A preferred reagent solution contains from 0.10 to 0.30 M borate buffer titrated to an initial pH of about 8.5 to about 9.5 and 0.05% to 0.10% of an indicator such as m-cresol purple. In a preferred embodiment a paper matrix is impregnated with an aqueous solution containing from 0.1 to 0.3M of borate buffer titrated to an initial pH above 6.5 prior to incorporation with the test composition. A preferred borate buffer for pretreatment is prepared from phenylboronic acid.

The test device is advantageously used by momentarily dipping it in a test sample or by otherwise introducing a test sample onto the carrier matrix, whereby a detectable colorimetric change results when glucose is present. Contact with the test sample can also be made by pipette, swab or spatula. Although dipping is a highly satisfactory method of contact when urine is used, a serum sample will normally require pipetting.

Semiquantitative glucose concentrations can be determined visually by comparison with an appropriate color chart or measurements can be made instrumentally by reflectance from either side of the device if a transparent support member is used.

A preferred embodiment for a glucose test device of the present invention is a self-indicating device which permits the determination of the concentration of glucose in an aqueous test sample without comparison to an additionally provided color chart. In fact, because of the basic chemistry of the reagents involved in this invention, a self-indicating device can be provided in which the only user determination necessary is the determination of the number of test means on a multipad test device which have changed color. A self-indicating device can be constructed so that each test means, when contacted with a glucose test sample at a concentration equal to or greater than the specified concentration for which that test means is designed to react, will change color to approximately the same color.

The self-indicating device is prepared by affixing a plurality of test matrices to a support member. Each test matrix is prepared by incorporating a test composition, designed to react with a different but predetermined concentration of glucose, with a carrier. The test composition can be formulated as described previously, however, usually the same chemical components will be incorporated with each matrix and the composition in each test matrix will differ only in the concentration of dihydroxide and the initial pH. In a preferred formulation for high range glucose, the self-indicating device is prepared by incorporating a plurality of test matrices with a pH indicator capable of providing a detectable colorimetric response and a borate buffer wherein the concentration of borate buffer and the initial pH of the borate buffer is different in each test matrix.

The self-indicating format is particularly preferred for the determination of glucose with a borate buffer. By counting the number of pads that change color, the user is able to tell the amount of glucose present without resorting to a color chart comparison. The pads can be arranged separately on a support such as Trycite or joined together. For a sample glucose concentration less than the concentration with which the test means is designed to react, there will be no color change. The user, given the information that a color change of one to two test means corresponds to a normal reading, while the change of three or more test means indicates a possible pathological condition, can take appropriate action or seek professional assistance without the need to compare the color of the pad with a color chart. Given the differences in color discrimination between different individuals and the differences in color discrimination in different lighting conditions, the use of the present invention in this format is particularly advantageous.

In the dihydroxide complexing system, the complexation of glucose with the dihydroxide releases a proton. Therefore, the pH of the system decreases. In a single (test means) pad system, the indicator changes color over the pH range produced by the complexation of glucose over the concentration range of glucose which the system is designed to determine. Usually an indicator with a pKa approximately mid-range in the pH range expected in the test is chosen. The decrease in pH with increased glucose can be moderated somewhat by setting the initial pH of the test means at a point which best moderates the pH change produced.

Most pH indicators change color over a fairly wide pH range, however over smaller pH ranges within that range the color visible to the eye is apparently the same. The concentration of dihydroxide and the initial pH can be chosen for each test means so that reaction with any concentration of glucose equal to or greater than that with which the test means is designed to react, the pH change produced by the complexation reaction takes the indicator to a point within that smaller pH range wherein the color is apparently the same to the naked eye. In a preferred embodiment using a borate buffer and cresol red, it has been found that while the hue of the reacted test means can be different (i.e., one reacted test means can provide a light gold while another reacted test means can provide a deep gold), the final color of test means designed to react with a concentration equal to or less than the test sample glucose concentration is the same. On the other hand, the color of test means designed to react with glucose concentrations greater than that of the test sample definitely remains the color of an unreacted test means (in the case of cresol red, the unreacted test means color is red). Indicators for use with a high range glucose self-indicating device should change color within the pH range of from about 6.5 to 12. For the self indicating format, it is preferred to use an indicator, such as cresol red or m-cresol purple, which has a defined color at more basic pH values (higher pH values) and changes fairly abruptly to a well defined and dramatically different color at lower pH values. A similar color change over a requisite pH range can be obtained with mixed indicator systems.

The following examples describe experiments which were performed in developing the present invention. A preferred self indicating format is described in Example 4. While the examples serve to illustrate the invention, they are not to be interpreted as limiting its scope, which is defined solely by the claims. One skilled in the art will be able to make such variations, substitutions and changes in the components of the composition and ingredients and reaction parameters as seem desirable.

| ABBREVIATIONS | |
|---|---|
| The following abbreviations are used in the examples. | |
| mg | milligram |
| mL | milliliter |
| dL | deciliter |
| M | molar |
| % | percent given in weight per 100 mL solution |
| PVP-K90 | poly(vinylpyrrolidone) average molecular weight 360,000 from GAF Corp., New York, N.Y. |
| m-cresol purple | meta-cresolsulfonephthalein |
| cresol red | o-cresolsulfonephthalein |
| neutral red | 2-methyl-3-amino-6-dimethyl aminophenazine |
| thymol blue | thymolsulfonepthalein |
| phenylphthalein | 3,3-bis(p-hydroxyphenyl)-phthalide |
| phenol red | phenolsulfonephthalein |
| bromothymol blue | dibromothymolsulfonephthalein |
| Klucel LF | hydroxypropyl cellulose |
| polyethylene glycol 4000 | polyethylene glycol, molecular weight 4000 |

EXAMPLES

1. Phenylboronic acid buffer pretreatment

Whatman 54 filter paper was immersed in an aqueous solution containing 0.2 M phenylboronic acid buffer, initial pH 9.05. The impregnated paper was then dried for 15 minutes at 60° C. in an air oven. The dried paper was immersed in an aqueous solution containing 0.25 M borate buffer, initial pH 9.05, and 0.08% m-cresol purple (sodium salt). A stock solution of 1% m-cresol purple in ethanol was used to prepare the impregnating solution. The borate buffer was prepared by dissolving boric acid in water, adjusting the pH to 9.05 with potassium hydroxide and diluting to the desired volume. The doubly impregnated paper was again dried for 15 minutes at 60° C. in an air oven.

A piece of the doubly dried paper was affixed to a polystyrene support member for convenient handling. The test devices were tested by dipping in aqueous test samples containing from 1000 mg/dL to 8,000 mg/dL (i.e., 1 gm/dL to 8 gm/dL) glucose. Data displayed in the drawing indicates good linear correlation between glucose concentration (gm/dL) and the strip reading.

2 No pretreatment

Whatman 54 filter paper was immersed in a solution containing:

| boric acid buffer (1M, initial pH 9.5) | 2.0 mL |
|---|---|
| PVP K90 (15%) | 1.0 mL |
| Phenol Red (1M) | 0.2 mL |
| Water | 10.0 mL |

The impregnated paper was dried for 15 minutes at 60° C. in an air oven and a piece of the dried paper was affixed to support members made of polystyrene. The finished test device provides good visual resolution between 1,000, 2,000, 3,000 and 5,000 mg/dL glucose. The color changes from red for negative (less than 1,000 mg/dL glucose) to yellow (5,000 mg/dL glucose).

3. Double Indicator system

A particularly preferred test device for the determination of high range glucose (i.e. concentrations of at least 1,000 milligrams per deciliter) in a urine test sample is prepared as follows:

| Solution 1 (10% acetone in water) | |
|---|---|
| phenylboronic acid buffer (initial pH 9.0) | 0.23M |
| dodecylbenzenesulfonic acid (sodium salt) | 0.04% |
| Solution 2 | |
| boric acid buffer (initial pH 9.0) | 0.30M |
| PVP-K 60 | 1.2% |
| polyethylene | 0.8% |

-continued

| | |
|---|---|
| glycol 4000 | |
| Klucel LF (in ethanol) | 0.4% |
| Tween 21 | 0.04% |
| Cresol Red | 0.03% |
| Bromothymol Blue (in ethanol) | 0.003% |

Solution 2 is made up in 10% acetone. The final solution contains 10% acetone and 10% ethanol.

Filter paper, such as Whatman 54 or E & D 204, is pretreated by dipping into solution 1 and drying. The dried pretreated paper is dipped into solution 2 and dried. The dual indicator system facilitates the semi-quantitative differentiation of glucose concentrations between 1,000 mg/dL and 10,000 mg/dL as the difference in colorimetric response between different concentration levels is greater. This is particularly desirable for a visually read test device.

4 Self-Indicating Glucose Device

A The indicator m-cresol purple was used to prepare a test device for the determination of 1, 2, 4 and 8 grams per deciliter glucose in urine.

Four pieces of Whatman 54 paper (10"×2" or 25.4 by 5.08 cm) were impregnated with 0.2 M phenyl borate at pH 9.0 and dried for 15 minutes at 50° C. Each piece was then treated with one of the following solutions:

| | | | | |
|---|---|---|---|---|
| Borate Concentration (M) (10 mL) | 0.2 | 0.4 | 0.6 | 0.8 |
| 1% m-Cresol Purple (mL) in Ethanol | 0.8 | 0.8 | 0.8 | 0.8 |
| pH | 9.0 | 9.2 | 9.4 | 9.6 |

The papers were again dried (15 minutes at 50° C.), applied to double-sided adhesive and slit into 1/5" (0.508 cm) ribbons. The ribbons were applied on Trycite in order of increasing borate concentration and pH (toward handle) and slit into 1/5" (0.508 cm) strips.

Dipped in a urine sample containing 6 grams per deciliter glucose, three test means changed color from purple to gold. Although the depth of the final gold color was different (i.e., slightly lighter gold to a deep gold) for each reacted test means, all the reacted pads designed to determine 6 gm/dL glucose or less were readily identified as a gold. The fourth test means, designed to react with 8 gm/dL glucose, remained purple.

B. A similar self-indicating device was prepared using cresol red as an indicator.

Four pieces of Whatman 54 paper (10"×2" or 25.4 by 5.08 cm) were treated with 0.1 M phenyl borate solution at an pH 8.0 and then dried for 15 minutes at 50° C. Each was then separately impregnated with one of the four different solutions:

| | | | | |
|---|---|---|---|---|
| Borate Concentration (M) (10 mL) | 0.2 | 0.4 | 0.6 | 0.8 |
| 0.5% Cresol Red in Water (mL) | 0.8 | 0.8 | 0.8 | 0.8 |

-continued

| | | | | |
|---|---|---|---|---|
| pH | 9.0 | 9.2 | 9.6 | 9.8 |

The test means were designed to react with 1, 2, 4 and 8 g/dL glucose for urine test samples respectively. Test devices were assembled as previously described. The self indicating device exhibited no color change (remained red) when dipped in a urine sample containing 0.5 gm/dL glucose. However, when dipped into a urine sample containing 3 gm/dL glucose, two pads changed color (to yellow).

Obviously, many modifications and variations of the invention as set forth can be made without departing from the spirit or scope of the invention.

What is claimed is:

1. A reagent test strip for the semiquantitative determination of glucose consisting essentially of:
   a paper matrix impregnated with a test composition wherein the test composition contains from 0.1 to 0.3 M of a borate dihydroxide component selected from the group consisting of boric acid, phenylboronic acid, p-nitrophenylboronic acid, 4-methoxyphenylboronic acid, α-naphthylboronic acid and naphthylboronic acid titrated to an initial pH above 6.5 prior to incorporation with a pH indicator capable of providing a colorimetric response in the pH range of 6.5 to 12, said indicator being selected from the group consisting of m-cresol purple, cresol red, neutral red, thymol blue, phenolphthalein, o-cresol phthalein, phenol red and bromothymol blue.

2. A self-indicating test device useful for the visual semiquantitative determination of glucose concentration in an aqueous test sample, said test device consisting essentially of:
   first and second paper matrices separately affixed to a support member wherein the first matrix is incorporated with a first reagent system and the second matrix is incorporated with a second reagent system,
   wherein each of said reagent systems is formed by impregnating the respective paper matrices with from 0.1 to 0.3 M of a borate dihydroxide component selected from the group consisting of boric acid, phenylboronic acid, p-nitrophenylboronic acid, 4-methoxyphenylboronic acid, α-naphthylboronic acid and naphthylboronic acid titrated to an initial pH above 6.5 prior to incorporation with a pH indicator capable of providing colorimetric response in the pH range of 6.5 to 12, said indicator being selected from the group consisting of m-cresol purple, cresol red, neutral red, thymol blue, phenolphthalein, o-cresol phthalein, phenol red and bromothymol blue; and
   wherein the first and second reagent systems are different such that the threshold pH which causes a response to glucose with respect to the first reagent system is different from the threshold pH which causes a response to glucose with respect to the second reagent system.

3. The self-indicating test device of claim 2 wherein the indicator is a dual indicator comprising bromothymol blue and cresol red.

* * * * *